(12) United States Patent
Ambarkhane et al.

(10) Patent No.: US 9,018,261 B2
(45) Date of Patent: Apr. 28, 2015

(54) CHOLINE SALT OF AN ANTI-INFLAMMATORY SUBSTITUTED CYCLOBUTENEDIONE COMPOUND

(75) Inventors: Ameet Vijay Ambarkhane, Horsham (GB); Arnaud Mauler, Mulhouse (FR); Carsten Timpe, Neuenberg (DE); Urs Baettig, Horsham (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/241,306

(22) PCT Filed: Aug. 31, 2012

(86) PCT No.: PCT/IB2012/054502
§ 371 (c)(1),
(2), (4) Date: Feb. 26, 2014

(87) PCT Pub. No.: WO2013/030803
PCT Pub. Date: Mar. 7, 2013

(65) Prior Publication Data
US 2014/0206768 A1    Jul. 24, 2014

Related U.S. Application Data

(60) Provisional application No. 61/530,516, filed on Sep. 2, 2011.

(51) Int. Cl.
A61K 31/18 (2006.01)
C07C 317/36 (2006.01)
C07C 311/48 (2006.01)
C07C 215/40 (2006.01)

(52) U.S. Cl.
CPC .............. C07C 317/36 (2013.01); A61K 31/18 (2013.01); C07C 311/48 (2013.01); C07C 215/40 (2013.01); C07C 2101/04 (2013.01)

(58) Field of Classification Search
CPC ...................................................... A61K 31/18
USPC ......................................................... 514/603
See application file for complete search history.

(56) References Cited

U.S. PATENT DOCUMENTS

| | | | |
|---|---|---|---|
| 5,506,252 | A | 4/1996 | Butera et al. |
| 5,840,764 | A | 11/1998 | Quagliato et al. |
| 6,166,050 | A | 12/2000 | Lombardo et al. |
| 7,132,445 | B2 | 11/2006 | Taveras et al. |
| 8,039,472 | B2 | 10/2011 | Bhalay et al. |
| 2004/0097547 | A1 | 5/2004 | Taveras |
| 2004/0106794 | A1 | 6/2004 | Taveras et al. |
| 2004/0147559 | A1 | 7/2004 | Taveras et al. |
| 2005/0209164 | A1 | 9/2005 | Bogen et al. |
| 2006/0084661 | A1 | 4/2006 | Palovich et al. |
| 2007/0021494 | A1 | 1/2007 | Taveras et al. |
| 2008/0200523 | A1 | 8/2008 | Murthi et al. |
| 2008/0221128 | A1 | 9/2008 | Gege et al. |
| 2008/0234266 | A1 | 9/2008 | Mederski et al. |
| 2008/0262096 | A1 | 10/2008 | Mederski et al. |
| 2010/0130642 | A1 | 5/2010 | Stanjek et al. |

FOREIGN PATENT DOCUMENTS

| | | |
|---|---|---|
| DE | 102005035741 | 2/2007 |
| DE | 102005035742 | 2/2007 |
| EP | 1197485 | 4/2002 |
| EP | 1674457 | 6/2006 |
| EP | 1818325 B1 | 2/2010 |
| WO | WO 96/15103 | 5/1996 |
| WO | WO 98/33763 | 8/1998 |
| WO | WO 02/42264 | 5/2002 |
| WO | WO 02/057230 | 7/2002 |
| WO | WO 02/062761 | 8/2002 |
| WO | WO 02/079122 | 10/2002 |
| WO | WO 02/083624 | 10/2002 |
| WO | WO 03/000245 | 1/2003 |
| WO | WO 03/080053 | 10/2003 |
| WO | WO 2004/011418 | 2/2004 |
| WO | WO 2005/075447 | 8/2005 |
| WO | WO 2006/032372 | 3/2006 |
| WO | WO 2006/072354 | 7/2006 |
| WO | WO 2006/084661 | 8/2006 |
| WO | WO 2006/088920 | 8/2006 |
| WO | WO 2008/005570 | 1/2008 |
| WO | WO 2008/109178 | 9/2008 |
| WO | WO 2008/148790 | 12/2008 |
| WO | WO 2009/005801 | 1/2009 |
| WO | WO 2009/005802 | 1/2009 |
| WO | WO 2009/012375 | 1/2009 |
| WO | WO 2009/073683 | 6/2009 |
| WO | WO 2010/003658 | 1/2010 |
| WO | WO 2010/015613 | 2/2010 |
| WO | WO 2010/017051 | 2/2010 |
| WO | WO 2010/063802 | 6/2010 |
| WO | WO 2010/091543 | 9/2010 |

OTHER PUBLICATIONS

Xie et al., "Structure-Activity Relationships of Novel, Highly Potent, Selective, and Orally Active CCR1 Antagonists" *Bioorganic and Medicinal Chemistry Letters* 17:3367-3372, 2007.

(Continued)

*Primary Examiner* — Raymond Henley, III
(74) *Attorney, Agent, or Firm* — Rona Nardone

(57) ABSTRACT

6-chloro-3-[2-(1-ethyl-propylamino)-3,4-dioxo-cyclobut-1-enylamino]-2-hydroxy-N-methoxy-N-methyl-benzene-sulfonamide choline, solid pharmaceutical compositions and oral dosage forms that contain said compound, and a method of using such compositions and oral dosage forms to treat people who have inflammatory, obstructive or allergic conditions and diseases are disclosed.

20 Claims, 1 Drawing Sheet

(56) References Cited

OTHER PUBLICATIONS

Lai et al., "Synthesis and Structure-Activity Relationships of new Disubstituted Phenyl-Containing 3,4-diamino-3-cyclobutene-1,2-diones as CXCR2 Receptor Antagonists" *Bioorganic and Medicinal Chemistry Letters* 18:1864-1868, 2008.

Butera et al., "Design and SAR of Novel Potassium Channel Openers Targeted for Urge Urinary Incontinence. 1. N-Cyanoguanidine Bioisosteres Possessing in Vivo Bladder Selectivity" *Journal of Medicinal Chemistry* 43(6):1187-1202, 2000.

Yu et al., "Synthesis and Structure-Activity Relationships of Heteroaryl Substituted-3,4-diamino-3-Cyclobut-3-ene-1,2-dione CXCR2/CXCR1 Receptor Antagonists" *Bioorganic and Medicinal Chemistry Letters* 18(4):1318-1322, 2008.

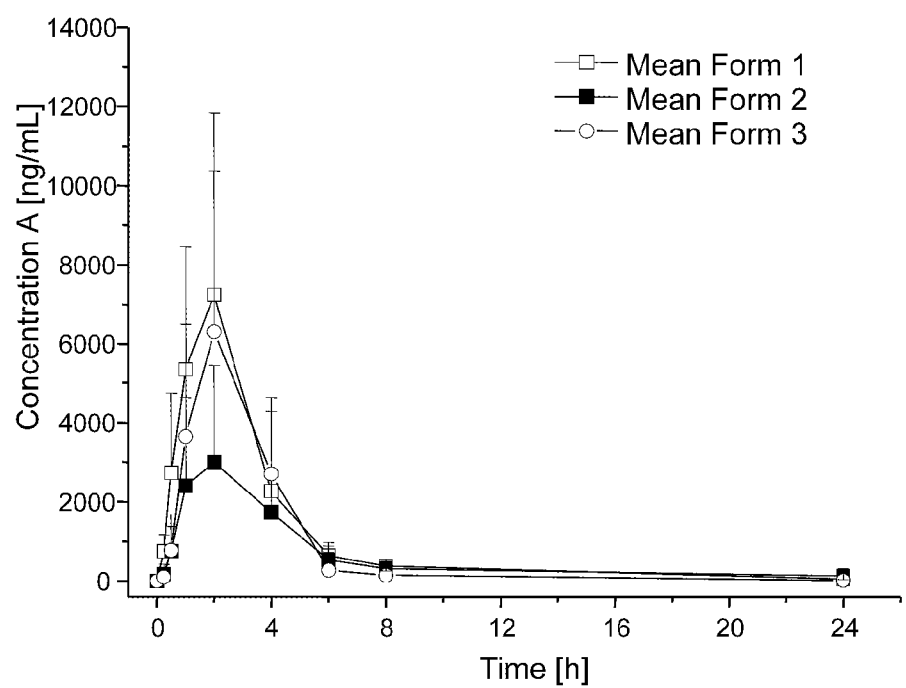

CHOLINE SALT OF AN ANTI-INFLAMMATORY SUBSTITUTED CYCLOBUTENEDIONE COMPOUND

CROSS-REFERENCE TO RELATED APPLICATIONS

This application is the U.S. National Stage of International Application No. PCT/IB2012/054502, filed Aug. 31, 2012, which claims the benefit of priority to U.S. Provisional Application No. 61/530,516, filed Sep. 2, 2011, the contents of which are incorporated herein by reference.

FIELD OF THE INVENTION

The present invention relates to a novel salt of a pharmaceutically active agent, solid pharmaceutical compositions and oral dosage forms for the delivery of said salt to patients in need thereof and the use of such solid pharmaceutical compositions and oral dosage forms.

BACKGROUND

Compound 6-chloro-3-[2-(1-ethyl-propylamino)-3,4-dioxo-cyclobut-1-enylamino]-2-hydroxy-N-methoxy-N-methyl-benzenesulfonamide and a method of preparing same have been disclosed in international patent application WO 2010/015613 as Example 8. Compound 6-chloro-3-[2-(1-ethyl-propylamino)-3,4-dioxo-cyclobut-1-enylamino]-2-hydroxy-N-methoxy-N-methyl-benzenesulfonamide is a pharmaceutically active agent and acts as a CXCR2 receptor antagonist and is useful in the treatment of inflammatory, obstructive or allergic conditions and diseases, for example for the treatment of chronic obstructive pulmonary disease (COPD).

Oral delivery of pharmaceutically active agents is generally the delivery route of choice, even when treating respiratory diseases, since it is convenient, relatively easy and generally painless resulting in greater patient compliance relative to other modes of delivery. However, biological, chemical and physical barriers such as poor solubility, varying pH in the gastrointestinal tract, powerful digestive enzymes and impermeable gastrointestinal membranes make oral delivery of some pharmaceutically active agents to mammals problematic or even impossible.

Compound 6-chloro-3-[2-(1-ethyl-propylamino)-3,4-dioxo-cyclobut-1-enylamino]-2-hydroxy-N-methoxy-N-methyl-benzenesulfonamide of formula I

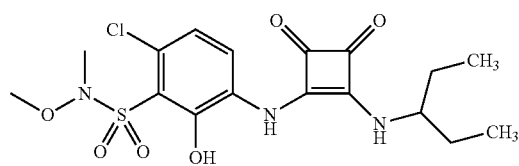

is a weakly acidic compound and is practically insoluble in aqueous solution at pH 1.0-7.0 as a free acid (<0.005 mg/ml).

Accordingly, there is a need to provide novel forms of 6-chloro-3-[2-(1-ethyl-propylamino)-3,4-dioxo-cyclobut-1-enylamino]-2-hydroxy-N-methoxy-N-methyl-benzenesulfonamide which show at least some superior characteristics over the free acid form. There is also a need for formulations which provide effective bioavailability of 6-chloro-3-[2-(1-ethyl-propylamino)-3,4-dioxo-cyclobut-1-enylamino]-2-hydroxy-N-methoxy-N-methyl-benzenesulfonamide in plasma.

The present invention provides such a novel salt form of 6-chloro-3-[2-(1-ethyl-propylamino)-3,4-dioxo-cyclobut-1-enylamino]-2-hydroxy-N-methoxy-N-methyl-benzenesulfonamide and formulation of same which solve the above problems or at least provide a useful alternative to the known salts and formulations of this compound.

SUMMARY OF THE INVENTION

In a first aspect, the present invention relates to the choline salt of 6-chloro-3-[2-(1-ethyl-propylamino)-3,4-dioxo-cyclobut-1-enylamino]-2-hydroxy-N-methoxy-N-methyl-benzenesulfonamide of formula II

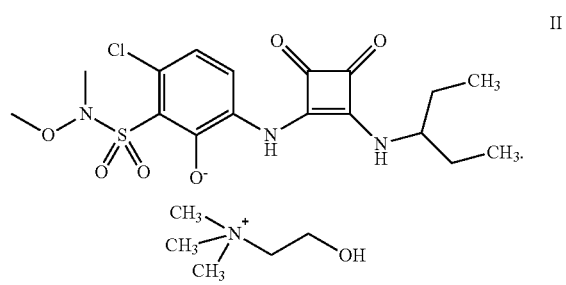

In this salt form 6-chloro-3-[2-(1-ethyl-propylamino)-3,4-dioxo-cyclobut-1-enylamino]-2-hydroxy-N-methyl-benzenesulfonamide is surprisingly more soluble in simulated gastric fluid than the free acid disclosed in WO 2010/015613.

In a second aspect, the invention relates to a solid pharmaceutical composition comprising
a) choline salt of 6-chloro-3-[2-(1-ethyl-propylamino)-3,4-dioxo-cyclobut-1-enylamino]-2-hydroxy-N-methyl-benzenesulfonamide;
b) an alkalizing agent;
c) a precipitation inhibiting agent; and
d) an additional pharmaceutically acceptable carrier.

As used herein, the term "alkalizing agent" is an agent capable of raising the pH of the micro-environment for 6-chloro-3-[2-(1-ethyl-propylamino)-3,4-dioxo-cyclobut-1-enylamino]-2-hydroxy-N-methoxy-N-methyl-benzenesulfonamide in the hydrated formulation to a pH greater than about its pKa (pKa=5.4). One skilled in the art will appreciate that acidic agents can also be used to adjust the pH of the alkalizing agent as long as the alkalizing agent as a whole raises the pH of the micro-environment in the hydrated formulation to greater than about the pKa of 6-chloro-3-[2-(1-ethyl-propylamino)-3,4-dioxo-cyclobut-1-enylamino]-2-hydroxy-N-methoxy-N-methyl-benzenesulfonamide. Suitable alkalizing agents include but are not limited to organic and inorganic basic compounds of a wide range of aqueous solubilities and molecular weights and mixtures thereof. Examples of inorganic basic salts include ammonium hydroxide, alkali metal salts, alkaline earth metal salts such as magnesium oxide, magnesium hydroxide, calcium hydroxide, sodium hydroxide, potassium hydroxide, aluminium hydroxide, potassium carbonate, sodium bicarbonate and the like and mixtures thereof. In particular, an alkalizing agent is selected from magnesium oxide, calcium carbonate, calcium phosphate and combinations thereof. More particularly, the alkalizing agent is magnesium oxide.

As used herein, the term "precipitation inhibiting agent" refers to salts, ions, carbohydrates, surfactants, amino acids, polymers and other compounds which, when present in solution, decrease the precipitation (crystallization) of 6-chloro-3-[2-(1-ethyl-propylamino)-3,4-dioxo-cyclobut-1-enylamino]-2-hydroxy-N-methoxy-N-methyl-benzenesulfonamide. Examples of precipitation inhibitors include but are not limited to polyvinyl pyrrolidone, for example those products known as PVP K30, PVP K29/32 and PVPP XL, and hydroxy propyl methyl cellulose (HPMC), for example those products known as PHARMACOAT® low viscous hypromellose-based water-soluble film coating agent.

As used herein, the term "additional pharmaceutically acceptable carrier" refers to conventional pharmaceutical carriers, such as disintegrants, diluents, lubricants, glidants and binders which are known to a person skilled in the galenic art, and which are added to the composition in addition to the alkalizing agent(s) and the precipitation inhibiting agent(s). For example, known disintegrants such as croscarmellose sodium, sodium starch glycolate and crospovidone may be used as additional pharmaceutically acceptable carriers\. In particular, an additional pharmaceutically acceptable carrier is selected from disintegrants, diluents, lubricants, glidants and binders. More particularly, the pharmaceutically acceptable carrier is selected from croscarmellose sodium, mannitol, microcrystalline cellulose, magnesium stearate and colloidal silicon dioxide.

As used herein, the term "oral dosage form" refers to physically discrete units suitable as unitary dosages for humans and other mammals, each unit containing a predetermined quantity of a therapeutic agent in association with one or more pharmaceutically acceptable carrier. Well-known oral dosage forms are for example tablets, capsules and caplets.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

The entire disclosure of each [United States patent and] international patent application mentioned in this patent specification is fully incorporated by reference herein for all purposes.

DESCRIPTION OF THE DRAWING

FIG. 1: A is 6-chloro-3-[2-(1-ethyl-propylamino)-3,4-dioxo-cyclobut-1-enylamino]-2-hydroxy-N-methoxy-N-methyl-benzenesulfonamide; the concentration [ng/mL] relates to the mean concentrations of A (ng/mL, mean±standard deviation) in plasma of male beagle dogs after administration of 63 mg/animal (calculated as free acid; n=5 dogs per treatment group) of A as capsules according to Example 3 (=Form 1), a solid dispersion formulation (=Form 2) and enteric coated beads (=Form 3).

DETAILED DESCRIPTION OF THE INVENTION

In a first aspect the present invention provides a novel salt of 6-chloro-3-[2-(1-ethyl-propylamino)-3,4-dioxo-cyclobut-1-enylamino]-2-hydroxy-N-methoxy-N-methyl-benzenesulfonamide, namely 6-chloro-3-[2-(1-ethyl-propylamino)-3,4-dioxo-cyclobut-1-enylamino]-2-hydroxy-N-methoxy-N-methyl-benzenesulfonamide choline of formula II.

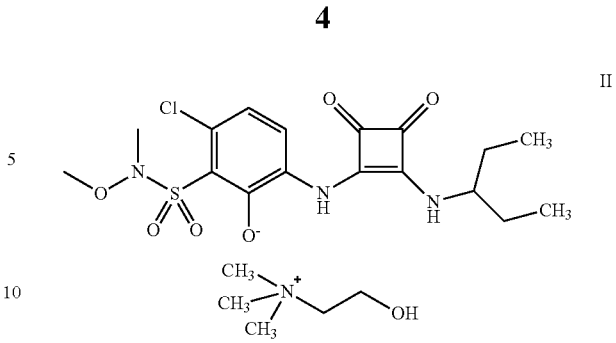

It was surprisingly found that the choline salt of 6-chloro-3-[2-(1-ethyl-propylamino)-3,4-dioxo-cyclobut-1-enylamino]-2-hydroxy-N-methoxy-N-methyl-benzenesulfonamide has superior solubility in simulated gastric fluid. Whereas the solubility of the free acid is 0.001 mg/ml in simulated gastric fluid at pH 1.2, the solubility of the choline salt is 8.018 mg/ml. Furthermore, the solubility of the choline salt in simulated gastric fluid is also significantly improved compared to other salts of 6-chloro-3-[2-(1-ethyl-propylamino)-3,4-dioxo-cyclobut-1-enylamino]-2-hydroxy-N-methoxy-N-methyl-benzenesulfonamide such as sodium, calcium, N,N-dimethyl-2-aminoethanol and N-(2-hydroxyethyl)pyrrolidine salts.

Furthermore, the hygroscopicity of the choline salt is much reduced compared with the free acid. The amount of water absorbed by the free acid is 2.4% and 2.8% by weight after 1 day at 80% and 92% humidity, respectively, and the amount of water absorbed by the choline salt is 0.7% and 0.6% by weight after 1 day at 80% and 92% humidity, respectively.

The choline salt has also a much improved dissolution rate at pH 1 and oral exposure when dosed at 10 mg/kg to male SPRAGUE DAWLEY® rats compared to the free acid form.

Although the choline salt of 6-chloro-3-[2-(1-ethyl-propylamino)-3,4-dioxo-cyclobut-1-enylamino]-2-hydroxy-N-methoxy-N-methyl-benzenesulfonamide has good solubility in gastric acidic conditions in the stomach, the choline salt of 6-chloro-3-[2-(1-ethyl-propylamino)-3,4-dioxo-cyclobut-1-enylamino]-2-hydroxy-N-methoxy-N-methyl-benzenesulfonamide readily converts in gastric acidic conditions into the free acid form which is poorly soluble. The result of this is poor bioavailability of 6-chloro-3-[2-(1-ethyl-propylamino)-3,4-dioxo-cyclobut-1-enylamino]-2-hydroxy-N-methoxy-N-methyl-benzenesulfonamide.

In a second aspect the present invention provides a solid pharmaceutical composition of 6-chloro-3-[2-(1-ethyl-propylamino)-3,4-dioxo-cyclobut-1-enylamino]-2-hydroxy-N-methoxy-N-methyl-benzenesulfonamide choline. The solid pharmaceutical composition comprises a) choline salt of 6-chloro-3-[2-(1-ethyl-propylamino)-3,4-dioxo-cyclobut-1-enylamino]-2-hydroxy-N-methoxy-N-methyl-benzenesulfonamide;
b) an alkalizing agent;
c) a precipitation inhibiting agent; and
d) an additional pharmaceutically acceptable carrier.

It was surprisingly found that this composition has an improved dissolution rate and an improved bioavailability as measured as AUC, mean $C_{max}$ and lower inter-animal variability denoted by the % CV (see Example 7, Table 1, FIG. 1).

It is particularly surprising that the mean concentration of 6-chloro-3-[2-(1-ethyl-propylamino)-3,4-dioxo-cyclobut-1-enylamino]-2-hydroxy-N-methoxy-N-methyl-benzenesulfonamide in plasma of male beagle dogs after oral administration of similar doses is higher when a composition according to the second aspect is used than when special delivery formulations are used such as enteric coated beads formulation or solid dispersion formulation (see Example 7, Table 1, FIG. 1).

In one embodiment (i) of the second aspect of the present invention, the alkalizing agent is selected from magnesium oxide, calcium carbonate, calcium phosphate and combinations thereof. Particularly, the alkalizing agent is magnesium oxide.

In one embodiment (ii) of the second aspect or embodiment (i) of the second aspect, the precipitation inhibiting agent is selected from polyvinylpyrrolidone and hydroxypropyl methyl cellulose. Particularly, the precipitation inhibiting agent is polyvinylpyrrolidone. More particularly, polyvinylpyrrolidone is selected from products known as PVP K30, PVP K29/32 and PVPP XL, even more particularly PVP K30.

In one embodiment (iii) of the second aspect or embodiment (i) or (ii) of the second aspect, the amount of alkalizing agent is in the range from about 5% to about 30% by weight of the total weight of solid pharmaceutical composition, particularly the amount of alkalizing agent is in the range from about 10% to about 20% by weight of the total weight of solid pharmaceutical composition, more particularly in the range from about 10% to about 15% by weight.

In one embodiment (iv) of the second aspect or embodiments (i) to (iii) of the second aspect, the amount of precipitation inhibiting agent is in the range from about 8% to about 20% by weight of the total weight of solid pharmaceutical composition, particularly in the range from about 10% to about 15% by weight.

In one embodiment (v) of the second aspect or embodiments (i) to (iv) of the second aspect, the additional pharmaceutically acceptable carrier is selected from disintegrants, diluents, lubricants, glidants and binders, or a mixture thereof.

In one embodiment (vi) of the second aspect or embodiments (i) to (v) of the second aspect, the invention relates to a solid pharmaceutical composition comprising
a) choline salt of 6-chloro-3-[2-(1-ethyl-propylamino)-3,4-dioxo-cyclobut-1-enylamino]-2-hydroxy-N-methoxy-N-methyl-benzenesulfonamide;
b) magnesium oxide;
c) polyvinylpyrrolidone; and
d) a mixture of croscarmellose sodium and mannitol.

In one particular embodiment (vii) of embodiment (vi) of the second aspect, the composition further comprises microcrystalline cellulose, magnesium stearate and colloidal silicon dioxide.

In a third aspect, the present invention relates to an oral dosage form comprising the composition according to the second aspect or embodiments (i)-(vii) of the second aspect.

In an embodiment (i) of the third aspect, the amount of the choline salt of 6-chloro-3-[2-(1-ethyl-propylamino)-3,4-dioxo-cyclobut-1-enylamino]-2-hydroxy-N-methoxy-N-methyl-benzenesulfonamide is from about 5 to about 100 mg on a dry basis calculated as the free acid.

In an embodiment (ii) of the third aspect, the amount of the choline salt of 6-chloro-3-[2-(1-ethyl-propylamino)-3,4-dioxo-cyclobut-1-enylamino]-2-hydroxy-N-methoxy-N-methyl-benzenesulfonamide is about 75 mg on a dry basis calculated as the free acid.

In another embodiment (iii) of the third aspect, the amount of the choline salt of 6-chloro-3-[2-(1-ethyl-propylamino)-3,4-dioxo-cyclobut-1-enylamino]-2-hydroxy-N-methoxy-N-methyl-benzenesulfonamide is about 25 mg on a dry basis calculated as the free acid.

In another embodiment (iv) of the third aspect, the amount of the choline salt of 6-chloro-3-[2-(1-ethyl-propylamino)-3,4-dioxo-cyclobut-1-enylamino]-2-hydroxy-N-methoxy-N-methyl-benzenesulfonamide is about 5 mg on a dry basis calculated as the free acid.

In a further embodiment (v) of the third aspect or embodiments (i)-(iv) of the third aspect, the dosage form is selected from a tablet, capsule and caplet, particularly a capsule. Such capsules may be prepared by a conventional blending process, for example in a diffusion blender and using appropriate sieving steps to enable a homogenous distribution of the ingredients. As a person skilled in the galenic art would know, the particle sizes of carriers should not differ too much from the particle size of the choline salt of 6-chloro-3-[2-(1-ethyl-propylamino)-3,4-dioxo-cyclobut-1-enylamino]-2-hydroxy-N-methoxy-N-methyl-benzenesulfonamide to avoid segregation during blending. The final blend can be filled manually or an automated capsule filling machine into hard gelatin, HPMC, starch or pullulan capsules.

In a fourth aspect, the present invention relates to a composition or oral dosage form according to the second and third aspect, respectively, for use in medicine, particularly for use in the treatment of conditions and diseases mediated by CXCR2, for example inflammatory, obstructive or allergic conditions and diseases, particularly chronic obstructive pulmonary airways disease (COPD), including chronic bronchitis or dyspnea associated therewith, emphysema, bronchiolitis obliterans syndrome and severe asthma.

In a fifth aspect, the present invention relates to a method of treating conditions and diseases mediated by CXCR2, for example inflammatory or allergic conditions and diseases, particularly chronic obstructive pulmonary airways disease (COPD), including chronic bronchitis or dyspnea associated therewith, emphysema, bronchiolitis obliterans syndrome and severe asthma, comprising administering to a person or mammal an effective amount of a composition or an oral dosage form according to the second and third aspect, respectively.

Additional embodiments and features are set forth in part in the description that follows, and in part will become apparent to those skilled in the art upon examination of the specification or may be learned by the practice of the invention.

This invention is further illustrated by the following examples which should not be construed as limiting.

EXPERIMENTAL

Example 1

Small scale preparation of choline salt of 6-chloro-3-[2-(1-ethyl-propylamino)-3,4-dioxo-cyclobut-1-enylamino]-2-hydroxy-N-methoxy-N-methyl-benzenesulfonamide Methanol (15.6 ml) was added under nitrogen at room temperature to 6-chloro-3-[2-(1-ethyl-propylamino)-3,4-dioxo-cyclobut-1-enylamino]-2-hydroxy-N-methoxy-N-methyl-benzenesulfonamide (4.8 g) to give a yellow suspension. This suspension was heated to 65±3° C. for 15 minutes at or near reflux. Choline hydroxide (2.78 mg) in methanol was added over 30 minutes. The dark brown solution was filtered and washed with methanol (3.6 ml). Isopropanol (12.3 ml) was added over 30 minutes to the dark brown solution and the whole was then cooled to 55° C. Seed crystals of 6-chloro-3-[2-(1-ethyl-propylamino)-3,4-dioxo-cyclobut-1-enylamino]-2-hydroxy-N-methoxy-N-methyl-benzenesulfonamide choline (3 mg) were added and the solution stirred until start of crystallisation. The solution was then cooled to 0° C. over two hours and stirred at that temperature for two hours.

The yellow suspension was filtered and washed with isopropanol (10 ml). The wet filter cake was dried in a vacuum oven overnight at 85° C.

Example 2

Preparation of choline salt of 6-chloro-3-[2-(1-ethyl-propylamino)-3,4-dioxo-cyclobut-1-enylamino]-2-hydroxy-N-methoxy-N-methyl-benzenesulfonamide Methanol (81.3 kg, 103 liters) was added under nitrogen to 6-chloro-3-[2-(1-ethyl-propylamino)-3,4-dioxo-cyclobut-1-enylamino]-2-hydroxy-N-methoxy-N-methyl-benzenesulfonamide (25.0 kg) to give a yellow suspension. This suspension was heated to 65±3° C. for 15 minutes. A solution of choline hydroxide (14.5 kg) in methanol (15.6 kg, 20 liters) was added to the suspension over a period of 30 minutes. The suspension was stirred for a further 60 minutes and then filtered and washed with methanol (3.3 kg, 4 liters). Isopropanol (64.1 kg, 82 liters) was then added over 30 minutes and the whole cooled to 55±2° C. Seed crystals of 6-chloro-3-[2-(1-ethyl-propylamino)-3,4-dioxo-cyclobut-1-enylamino]-2-hydroxy-N-methoxy-N-methyl-benzenesulfonamide choline (0.016 kg) were added and the suspension stirred at 55±2° C. before cooling down to 0±2° C. over 2 hours. The suspension was stirred for a further 2 hours before being centrifuged, washed with isopropanol (52.1 kg, 67 liters), filtered and the obtained crystals (25.4 kg) dried.

Example 3

63 mg capsule (calculated as free acid) of choline salt of 6-chloro-3-[2-(1-ethyl-propylamino)-3,4-dioxo-cyclobut-1-enylamino]-2-hydroxy-N-methoxy-N-methyl-benzenesulfonamide A pharmaceutical composition was prepared in the manner described in Example 1 from the ingredients listed in the following table and filled into capsules:

| Ingredient | Amount (mg) | % | Function |
|---|---|---|---|
| choline salt of 6-chloro-3-[2-(1-ethyl-propylamino)-3,4-dioxo-cyclobut-1-enylamino]-2-hydroxy-N-methoxy-N-methyl-benzenesulfonamide | 78.06 | 22.3 | Active ingredient |
| PVP K30 | 42.00 | 12.0 | Precipitation inhibiting agent |
| Magnesium oxide | 42.00 | 12.0 | Alkalizing agent |
| Cellulose MK GR | 42.3 | 12.1 | Filling agent, diluent |
| Mannitol SD200 | 110.64 | 31.6 | Diluent |
| Na-CMC XL (AC-DI-SOL) | 28.00 | 8.0 | Disintegrant |
| Aerosil ® 200 fumed silica | 1.75 | 0.5 | Glidant |
| magnesium stearate | 5.25 | 1.5 | Lubricant |
| capsule fill weight | 350.00 | 100 | |

Example 4

75 mg capsule (calculated as free acid) of choline salt of 6-chloro-3-[2-(1-ethyl-propylamino)-3,4-dioxo-cyclobut-1-enylamino]-2-hydroxy-N-methoxy-N-methyl-benzenesulfonamide A pharmaceutical composition was prepared in the manner described in Example 1 from the ingredients listed in the following table and filled into capsules:

| Ingredient | Amount (mg) | % | Function |
|---|---|---|---|
| choline salt of 6-chloro-3-[2-(1-ethyl-propylamino)-3,4-dioxo-cyclobut-1-enylamino]-2-hydroxy-N-methoxy-N-methyl-benzenesulfonamide | 92.93 | 25.1 | Active ingredient |
| PVP K30 | 44.40 | 12.0 | Precipitation inhibiting agent |
| magnesium oxide | 50.00 | 13.5 | Alkalizing agent |
| Cellulose MK GR | 55.09 | 14.9 | Filling agent, diluent |
| Mannitol SD200 | 105.38 | 28.5 | Diluent |
| Na-CMC XL (AC-DI-SOL) | 14.80 | 4.0 | Disintegrant |
| Aerosil ® 200 fumed silica | 1.85 | 0.5 | Glidant |
| magnesium stearate | 5.55 | 1.5 | Lubricant |
| capsule fill weight | 370.00 | 100 | |
| empty capsule shell | 96.00 | | |
| Total capsule weight | 466.00 | | |

Example 5

25 mg capsule (calculated as free acid) of choline salt of 6-chloro-3-[2-(1-ethyl-propylamino)-3,4-dioxo-cyclobut-1-enylamino]-2-hydroxy-N-methoxy-N-methyl-benzenesulfonamide A pharmaceutical composition was prepared in the manner described in Example 1 from the ingredients listed in the following table and filled into capsules:

| Ingredient | Amount (mg) | % | Function |
|---|---|---|---|
| choline salt of 6-chloro-3-[2-(1-ethyl-propylamino)-3,4-dioxo-cyclobut-1-enylamino]-2-hydroxy-N-methoxy-N-methyl-benzenesulfonamide | 30.98 | 8.4 | Active ingredient |
| PVP K30 | 44.40 | 12.0 | Precipitation inhibiting agent |
| magnesium oxide | 50.00 | 13.5 | Alkalizing agent |
| Cellulose MK GR | 72.22 | 19.5 | Filling agent, diluent |
| Mannitol SD200 | 150.20 | 40.6 | Diluent |
| Na-CMC XL (AC-DI-SOL) | 14.80 | 4.0 | Disintegrant |
| Aerosil ® 200 fumed silica | 1.85 | 0.5 | Glidant |
| magnesium stearate | 5.55 | 1.5 | Lubricant |
| capsule fill weight | 370.00 | 100 | |
| empty capsule shell | 96.00 | | |
| Total capsule weight | 466.00 | | |

Example 6

5 mg capsule (calculated as free acid) of choline salt of 6-chloro-3-[2-(1-ethyl-propylamino)-3,4-dioxo-cyclobut-1-enylamino]-2-hydroxy-N-methoxy-N-methyl-benzenesulfonamide

| A pharmaceutical composition was prepared in the manner described in Example 1 from the ingredients listed in the following table and filled into capsules: Ingredient | Amount (mg) | % | Function |
|---|---|---|---|
| choline salt of 6-chloro-3-[2-(1-ethyl-propylamino)-3,4-dioxo-cyclobut-1-enylamino]-2-hydroxy-N-methoxy-N-methyl-benzenesulfonamide | 6.20 | 1.7 | Active ingredient |
| PVP K30 | 44.40 | 12.0 | Precipitation inhibiting agent |
| magnesium oxide | 50.00 | 13.5 | Alkalizing agent |
| Cellulose MK GR | 64.28 | 17.4 | Filling agent, diluent |
| Mannitol SD200 | 168.12 | 45.4 | Diluent |
| Na-CMC XL (AC-DI-SOL) | 29.60 | 8.0 | Disintegrant |
| Aerosil ® 200 fumed silica | 1.85 | 0.5 | Glidant |
| magnesium stearate | 5.55 | 1.5 | Lubricant |
| capsule fill weight | 370.00 | 100 | |
| empty capsule shell | 96.00 | | |
| Total capsule weight | 466.00 | | |

Example 7

Pharmacokinetic studies of the choline salt of 6-chloro-3-[2-(1-ethyl-propylamino)-3,4-dioxo-cyclobut-1-enylamino]-2-hydroxy-N-methoxy-N-methyl-benzenesulfonamide Male beagle dogs were administered oral single doses of capsules (63 mg choline salt of 6-chloro-3-[2-(1-ethyl-propylamino)-3,4-dioxo-cyclobut-1-enylamino]-2-hydroxy-N-methoxy-N-methyl-benzenesulfonamide per capsule calculated as free acid) according to Example 3 (=Form 1), a solid dispersion formulation (=Form 2) and enteric coated beads (=Form 3). The dogs were pretreated with pentagastrine (6 μg/kg) in order to lower the pH in the stomach and mimic more acidic conditions in humans. Three treatment groups (n=5 dogs per treatment group) were used for each Form of administration and the parameters measured are based on plasma concentrations. Table 1 summarizes the pharmacokinetic parameters for each of the three treatment groups.

TABLE 1

| PK parameter | Form 1 | Form 2 | Form 3 |
|---|---|---|---|
| $T_{max}$ (h)$^a$ | 2 [1-2] | 2 [1-4] | 2 [1-2] |
| $C_{max}$ (ng/mL) | 7510 ± 4490 | 3300 ± 2110 | 6440 ± 3860 |
| $C_{max}$/dose ((ng/mL)/(mg/kg)) | 1030 ± 588 | 454 ± 283 | 842 ± 516 |
| AUClast (h ng/mL) | 25600 ± 13200 | 14900 ± 8320 | 19800 ± 12700 |
| AUClast/dose ((h ng/mL)/(mg/kg)) | 3480 ± 1750 | 2040 ± 1090 | 2570 ± 1650 |

$^a$median [range]

The mean dose normalized AUClast of Form 1 was 1.7 and 1.3 times higher than the one of Form 2 and 3, respectively, with no impact on the $T_{max}$.

The systemic exposure of the choline salt of 6-chloro-3-[2-(1-ethyl-propylamino)-3,4-dioxo-cyclobut-1-enylamino]-2-hydroxy-N-methoxy-N-methyl-benzenesulfonamide in the dogs using Form 1, 2 and 3 was compared with the systemic exposure after intravenous administration (912±126 ng h/mL at 0.3 mg/kg). Oral bioavailabilies of 116% for Form 1, 75% for Form 2 and 85% for Form 3 was calculated.

The invention claimed is:

1. A solid pharmaceutical composition comprising
   a) choline salt of 6-chloro-3-[2-(1-ethyl-propylamino)-3,4-dioxo-cyclobut-1-enylamino]-2-hydroxy-N-methoxy-N-methyl-benzenesulfonamide;
   b) an alkalizing agent;
   c) a precipitation inhibiting agent; and
   d) an additional pharmaceutically acceptable carrier.

2. The composition according to claim 1, wherein the alkalizing agent is selected from magnesium oxide, calcium carbonate, calcium phosphate and combinations thereof.

3. The composition according to claim 1, wherein the alkalizing agent is magnesium oxide.

4. The composition according to claim 1, wherein the precipitation inhibiting agent is selected from polyvinylpyrrolidone and hydroxypropyl methyl cellulose.

5. The composition according to claim 1, wherein the precipitation inhibiting agent is polyvinylpyrrolidone.

6. The composition according to claim 5, wherein polyvinylpyrrolidone is selected from PVP K30, PVP K29/32 and PVPP XL, in particular PVP K30.

7. The composition according to claim 2, wherein the amount of alkalizing agent is in the range from about 5% to about 30% by weight of the total weight of solid pharmaceutical composition.

8. The composition according to claim 7, wherein the amount of alkalizing agent is in the range from about 10% to about 20% by weight of the total weight of solid pharmaceutical composition.

9. The composition according to claim 1, wherein the amount of precipitation inhibiting agent is in the range from about 8% to about 20% by weight of the total weight of solid pharmaceutical composition.

10. The composition according to claim 1, wherein the additional pharmaceutically acceptable carrier is selected from disintegrants, diluents, lubricants, glidants and binders.

11. The composition according to claim 1 comprising
    a) choline salt of 6-chloro-3-[2-(1-ethyl-propylamino)-3,4-dioxo-cyclobut-1-enylamino]-2-hydroxy-N-methoxy-N-methyl-benzenesulfonamide;
    b) magnesium oxide;
    c) polyvinylpyrrolidone; and
    d) a mixture of croscarmellose sodium and mannitol.

12. The composition according to claim 11 further comprising microcrystalline cellulose, magnesium stearate, colloidal silicon dioxide, or a mixture of these.

13. An oral dosage form comprising the composition according to claim 1, wherein the amount of the choline salt of 6-chloro-3-[2-(1-ethyl-propylamino)-3,4-dioxo-cyclobut-1-enylamino]-2-hydroxy-N-methoxy-N-methyl-benzenesulfonamide is from about 5 to about 100 mg on a dry basis calculated as the free acid.

14. The oral dosage form according to claim 13 wherein the amount of the choline salt of 6-chloro-3-[2-(1-ethyl-propylamino)-3,4-dioxo-cyclobut-1-enylamino]-2-hydroxy-N-methoxy-N-methyl-benzenesulfonamide is about 75 mg on a dry basis calculated as the free acid.

15. The oral dosage form according to claim 13 wherein the amount of the choline salt of 6-chloro-3-[2-(1-ethyl-propylamino)-3,4-dioxo-cyclobut-1-enylamino]-2-hydroxy-N- methoxy-N-methyl-benzenesulfonamide is about 25 mg on a dry basis calculated as the free acid.

16. The oral dosage form according to claim 13 wherein the amount of the choline salt of 6-chloro-3-[2-(1-ethyl-propylamino)-3,4-dioxo-cyclobut-1-enylamino]-2-hydroxy-N-methoxy-N-methyl-benzenesulfonamide is about 5 mg on a dry basis calculated as the free acid.

17. The oral dosage form according to claim 13, wherein the dosage form is selected from a tablet, a capsule and a caplet.

18. The oral dosage form according to claim 17, wherein the dosage from is a hard capsule.

19. A method to treat chronic obstructive pulmonary airways disease (COPD), chronic bronchitis or dyspnea associated with COPD, emphysema, bronchiolitis obliterans syndrome or severe asthma, comprising administering an effective amount of the compound according to claim 1, or the composition according to claim 2.

20. A method to treat chronic obstructive pulmonary airways disease (COPD), chronic bronchitis or dyspnea associated with COPD, emphysema, bronchiolitis obliterans syndrome or severe asthma, comprising administering to a person or mammal an effective amount of the oral dosage form according to claim 13.

* * * * *